United States Patent [19]

Zeh

[11] 4,118,987
[45] Oct. 10, 1978

[54] DEVICE FOR TAKING LIQUID SAMPLES

[75] Inventor: Horst Zeh, Karlsruhe, Fed. Rep. of Germany

[73] Assignee: Gesellschaft zur Wiederaufarbeitung von Kernbrennstoffen mbH, Eggenstein-Leopoldshafen, Fed. Rep. of Germany

[21] Appl. No.: 785,182

[22] Filed: Apr. 6, 1977

[30] Foreign Application Priority Data

Apr. 6, 1976 [DE] Fed. Rep. of Germany ....... 2614787

[51] Int. Cl.² .............................................. G01N 1/20
[52] U.S. Cl. ................................................. 73/422 R
[58] Field of Search .................. 73/421 R, 421 B, 422

[56] References Cited

U.S. PATENT DOCUMENTS

| | | | |
|---|---|---|---|
| 2,693,705 | 11/1954 | Casler | 73/421 B |
| 3,383,923 | 5/1968 | Conche et al. | 73/421 B |
| 3,872,730 | 3/1975 | Ringrose et al. | 73/421 B |

*Primary Examiner*—S. Clement Swisher
*Attorney, Agent, or Firm*—Spencer & Kaye

[57] ABSTRACT

A device for taking liquid samples from a liquid circuit has a needle head housing formed of an outer component and an inner component readily detachable from the outer component for easy replacement. The outer component includes inlet and outlet ports to be inserted in the liquid circuit. The inner component includes a flow passage aligned with the inlet and outlet ports of the outer component, a pressure reducing arrangement for generating a pressure drop of the liquid flowing through the passage and two hollow needles supported in the inner component and projecting outwardly therefrom. The needles have first ends that communicate with the passage in the inner component at locations where different liquid pressures prevail and second ends which are insertable into a sampling vessel.

6 Claims, 2 Drawing Figures

DEVICE FOR TAKING LIQUID SAMPLES

BACKGROUND OF THE INVENTION

This invention relates to a device for taking liquid samples from a liquid circuit and is of the type which includes a needle head housing which is inserted in the circuit and through which the liquid flows. The housing includes arrangements for generating a pressure drop between a liquid inlet and a liquid outlet and there are further provided, at two locations of different operational pressure, hollow needles each having a terminal opening insertable into a sampling vessel.

Devices of the above-outlined type serve in particular for the taking of radioactive or toxic liquid samples which very frequently also include solid particles. Because of this circumstance the hollow needles and the immediately adjoining zones tend to be obstructed by such particles. In order to eliminate operational disturbances arising from such obstructions, reverse flow rinsing arrangements or filters may be provided. In case the device is associated with a reverse flow rinsing device, delays occur in the sample taking when the unclogging (rinsing) operation is performed and further, it is not always possible to eliminate the obstructions. Consequently, often the entire needle head has to be replaced. In case filters are used, the latter have to be frequently replaced because of clogging.

SUMMARY OF THE INVENTION

It is an object of the invention to provide an improved liquid sample taking device in which the maintenance of the needle head housing is facilitated and its service life increased. In particular, in the device according to the invention, the replacement of obstruction-prone components is facilitated and the risk of clogging is reduced.

This object and others to become apparent as the specification progresses, are accomplished by the invention, according to which, briefly stated, the device for taking liquid samples from a liquid circuit has a needle head housing formed of an outer component and an inner component readily detachable from the outer component for easy replacement. The outer component includes inlet and outlet ports to be inserted in the liquid circuit. The inner component includes a flow passage aligned with the inlet and outlet ports of the outer component, a pressure reducing arrangement for generating a pressure drop of the liquid flowing through the passage and two hollow needles supported in the inner component and projecting outwardly therefrom. The needles have first ends that communicate with the passage in the inner component at locations where different liquid pressures prevail and second ends which are insertable into a sampling vessel.

The invention thus provides that the components likely to be involved in operational malfunctions are combined into a single, easily replaceable structural unit. Upon piercing the hollow needles when clogged, any solid plugging particles may be removed.

The conical shape of the housing components facilitates a remote-controlled replacement which is of particular advantage in case radioactive or toxic materials are handled. In case the inner component is made of a synthetic material such as polyethylene and the outer component is made of metal, such as high-grade steel, the connection is sufficiently self-locking (by frictional engagement) so that no additional securing means such as screws or the like are needed.

DESCRIPTION OF THE PREFERRED EMBODIMENT

Figure 1:
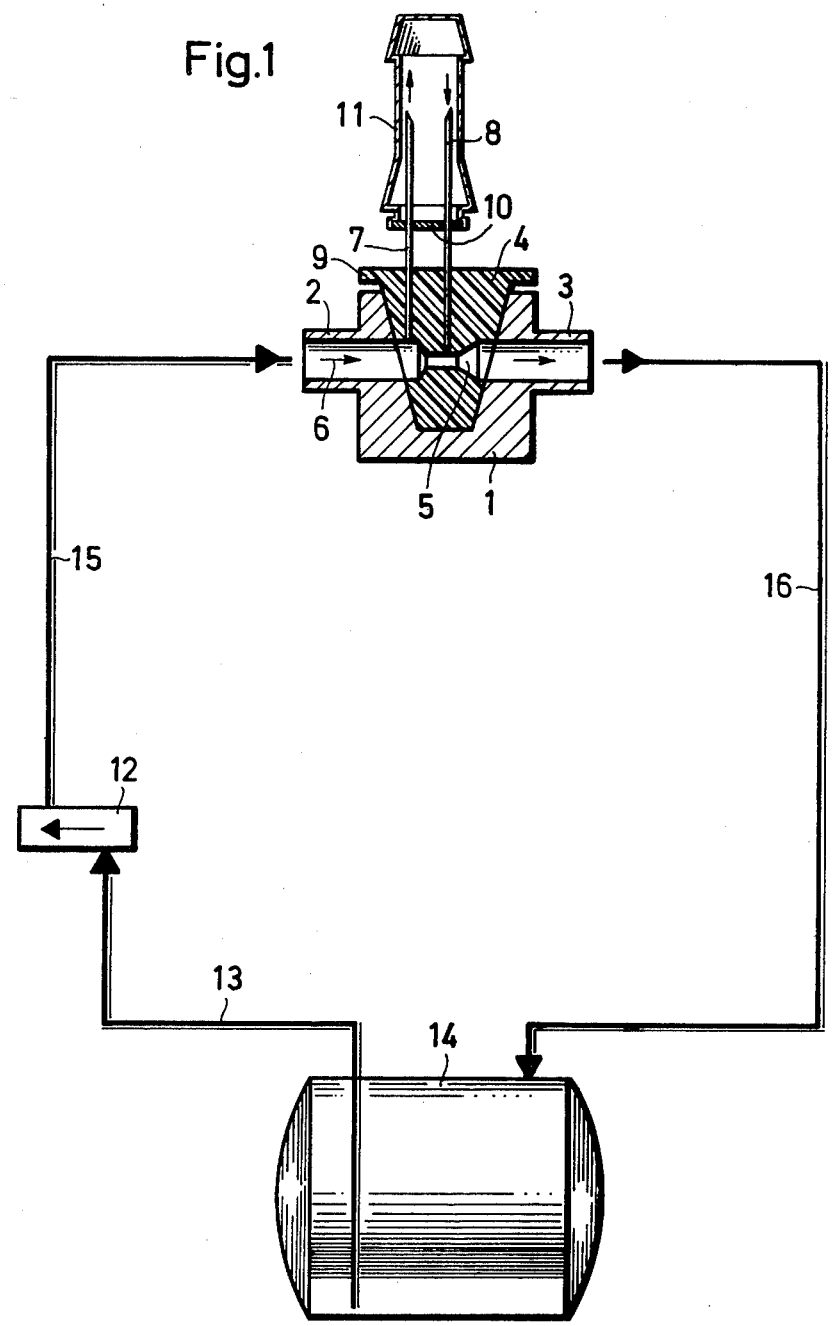
FIG. 1 is a schematic longitudinal sectional view of a preferred embodiment of a needle head housing associated with a sampling vessel and a liquid circuit from which the sample is to be taken.

Turning now to FIG. 1, the needle head housing shown therein comprises an outer component 1 made, for example, of high-grade steel and provided with inlet and outlet ports 2 and 3, respectively. The needle head housing further has an inner component 4 made, for example, of a synthetic material and having a through-going channel (flow passage) formed as a venturi nozzle 5. The latter is aligned with the inlet and outlet ports 2 and 3 of the outer housing component 1. Two parallel spaced, hollow needles 7 and 8 are supported in, and project outwardly from the component 4. The needle 7 communicates with the venturi 5 at the inlet side (where the venturi nozzle has a relatively large cross section), whereas the needle 8 communicates with the venturi 5 at the smallest cross section thereof, downstream of the needle 7, as viewed in the direction of liquid flow. The needles 7 and 8 extend perpendicularly to the principal liquid stream 6 passing through the needle head housing. The housing component 1 has an outwardly open, inwardly tapering conical cavity into which fits, in a conforming manner, the inner housing component 4 by virtue of its conically tapering, plug-like shape. The inner component 4 has an external flange 9 adapted to be engaged by a manipulator to made possible a remote controlled removal of the component 4 from, or its insertion into the component 1. The component 4, when inserted into the component 1, is held in the latter by friction, which effects an operationally safe connection during operation, but which is readily disconnectable by the manipulator.

It is thus seen that the outer housing component 4 combines into a readily replaceable structural unit all parts of the device that are likely to malfunction, for example, due to clogging by solid particles.

In the description that follows the sample taking operation will be set forth.

The diaphragm closure 10 of the sample collecting vessel 11 is pierced through by the upwardly oriented points of the hollow needles 7 and 8. A liquid drive arrangement 12, such as a jet pump draws liquid through a suction conduit 13 from a container 14 and drives the liquid through a pressure conduit 15 into the needle head housing 1, 4 from which the liquid is returned through a return conduit 16 into the container 14. During this liquid flow, in the needle 8 there is generated a pressure that is lower than that prevailing in the needle 7 so that the sampling vessel 11 is charged and subsequently rinsed by the liquid. After the proper rinsing period the charged sampling vessel 11 may be pulled off the needles 7 and 8. The liquid flow circuit has a pressure which is lower than that of the environment so that even after removal of the sampling vessel 11, no liquid can escape from the needle head housing through the needles.

Figure 2:
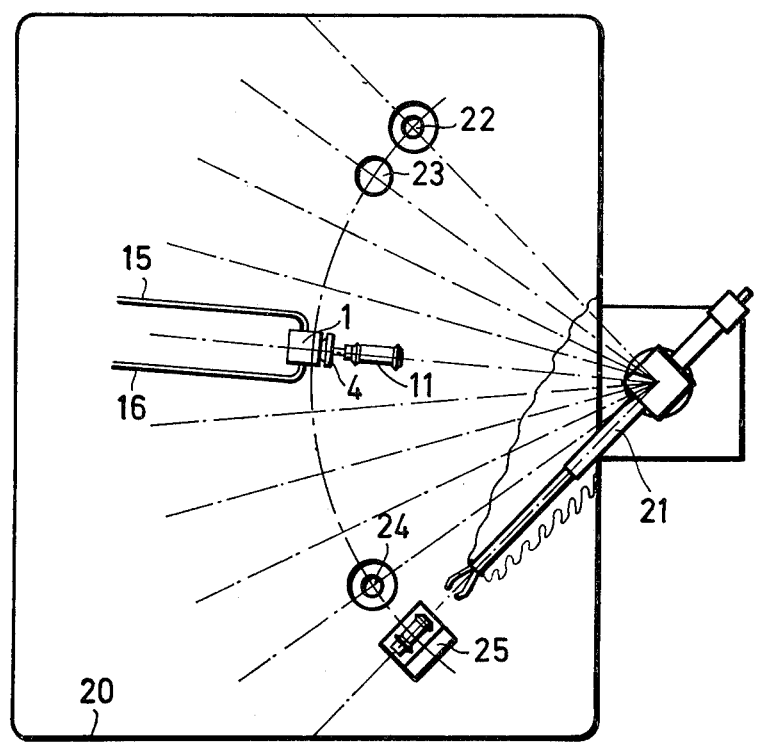
FIG. 2 is a schematic top plan view of a sample taking station operated by remote control.

Turning now to FIG. 2, there is schematically shown a sample taking station provided with a plurality of needle head housings 1, 4 each associatd with a separate conduit assembly 15 and 16. The needle head housings are arranged in a gastight box 20 which, in turn, is disposed in the operational range of a pivotally supported programmable rod manipulator 21. For the sake of clarity, only a single needle head housing with the associated conduits is shown, others are illustrated only symbolically by radially extending dash-dot lines. In addition, in the box 20, there are provided four further stations to be served by the manipulator 21, namely a needle head removal station 22, a needle head supply station 23, a dispatch tube station 24 to receive or discharge the sampling vessels 11, as well as a storage magazine 25 for the sampling vessels. The manipulator 21 removes one sampling vessel 11 from the magazine 25 and forwards it to a preprogrammed station for inserting it on the needle head 1, 4. Subsequent to rinsing and charging, the sampling vessel 11 is forwarded to the dispatch tube station 24 where it is removed from the box 20. A replacement of the needle head housing component 4 is effected in a similar manner by means of the manipulator 21, cooperating with the stations 22 and 23.

It will be understood that the above description of the present invention is susceptible to various modifications, changes and adaptations, and the same are intended to be comprehended within the meaning and range of equivalents of the appended claims.

What is claimed is:

1. In a device for taking liquid samples from a liquid circuit, including a needle head housing provided with a throughgoing flow passage having inlet and outlet ports and arranged to be inserted in the liquid circuit to provide liquid flow through the flow passage; pressure reducing means arranged between the passage inlet and the passage outlet for generating a pressure drop of the liquid in the passage; and two spaced hollow needles supported in the needle head housing; each needle having a first and a second end; the first needle ends communicating with the passage at locations where different fluid pressures prevail during operation; the second needle ends being insertable into a sampling vessel; the improvement wherein said needle head housing is formed of an outer component containing one part of said passage including said inlet and said outlet ports and an inner component including means for releasably attaching said inner component to said outer component; said inner component containing the other part of said passage, said pressure reducing means and said hollow needles.

2. A device as defined in claim 1, wherein said hollow needles directly join said pressure reducing means and are perpendicular to said flow passage.

3. A device as defined in claim 1, wherein said inner component has the shape of a conically tapering plug and said outer component has a conically inwardly tapering, outwardly open cavity for form-fittingly receiving said inner component.

4. A device as defined in claim 3, wherein said outer component is a metal and said inner component is a synthetic material.

5. A device as defined in claim 1, wherein said pressure reducing means includes a venturi nozzle having a relatively large cross section and, downstream thereof, a relatively small cross section; one of said needles communicating with said venturi nozzle at a location of said relatively large cross section and the other of said needles communicating with said venturi nozzle at a location of said relatively small cross section.

6. A device as defined in claim 1, wherein said hollow needles project outwardly from said inner housing component for insertion into a sampling vessel externally of said needle head housing.

* * * * *